United States Patent
Guo et al.

(10) Patent No.: US 10,259,771 B2
(45) Date of Patent: Apr. 16, 2019

(54) VEGETABLE OIL POLYOL AND THE PREPARATION METHOD AND THE APPLICATION THEREOF

(71) Applicant: NANJING TECH UNIVERSITY, Nanjing (CN)

(72) Inventors: Kai Guo, Nanjing (CN); Zheng Fang, Nanjing (CN); Dong Ji, Nanjing (CN); Junjie Tao, Nanjing (CN); Xin Li, Nanjing (CN); Li Wan, Nanjing (CN); Ning Zhu, Nanjing (CN); Kai Zhang, Nanjing (CN); Pingkai Ouyang, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 203 days.

(21) Appl. No.: 15/506,686

(22) PCT Filed: Jan. 28, 2016

(86) PCT No.: PCT/CN2016/072485
§ 371 (c)(1),
(2) Date: Feb. 24, 2017

(87) PCT Pub. No.: WO2017/080115
PCT Pub. Date: May 18, 2017

(65) Prior Publication Data
US 2018/0222841 A1 Aug. 9, 2018

(30) Foreign Application Priority Data

Nov. 11, 2015 (CN) .......................... 2015 1 0767650

(51) Int. Cl.
| | | |
|---|---|---|
| *C08G 18/36* | (2006.01) |
| *C07C 67/31* | (2006.01) |
| *C08G 18/67* | (2006.01) |
| *C08G 101/00* | (2006.01) |

(52) U.S. Cl.
CPC .............. *C07C 67/31* (2013.01); *C08G 18/36* (2013.01); *C08G 18/67* (2013.01); *C08G 2101/0025* (2013.01)

(58) Field of Classification Search
CPC ........ C07C 67/31; C08G 18/36; C08G 18/67; C08G 2101/0025
See application file for complete search history.

(56) References Cited

FOREIGN PATENT DOCUMENTS

CN 103274930 A * 9/2013

* cited by examiner

*Primary Examiner* — John M Cooney
(74) *Attorney, Agent, or Firm* — CBM Patent Consulting, LLC

(57) ABSTRACT

A preparation method of vegetable oil polyol, which is obtains by carrying out allylic oxidation treatment of vegetable oil, increasing the content of hydroxyl group in the product and then one step reaction between epoxidation and ring-opening. At the same time, the present invention also discloses novel vegetable oil polyol made by the preparation method and the application of the vegetable oil polyol in preparation of polyurethane foam material. Compared with the prior art, the method has the advantages of simple operation, low energy consumption and low side reaction occurrence rate.

8 Claims, 1 Drawing Sheet

VEGETABLE OIL POLYOL AND THE PREPARATION METHOD AND THE APPLICATION THEREOF

This application is the U.S. national phase of International Application No. PCT/CN2016/072485 filed on 28 Jan. 2016 which designated the U.S. and claims priority to Chinese Application Nos. CN201510767650.3 filed on 11 Nov. 2015, the entire contents of each of which are hereby incorporated by reference.

TECHNICAL FIELD

The present invention belongs to chemical engineering technical filed, in particular to a vegetable oil polyol and the preparation method and the application thereof.

BACKGROUND

A polyurethane material is a polymer having a repeating structural unit of a carbamic acid ester segment made by an isocyanate reacts with a polyol. Wherein, the international market of isocyanate tends to be stable, mainly MDI and TDI two types, supply and demand tends to balance and the production process is relatively perfect; and polyurethane polyol variety, currently on the market dominated polyols mainly for the high functionality polyether polyol obtained by reacting a hydroxy compound and an amine compound with epoxy propane or ethylene oxide, in addition, there are polyester polyol, modified graft polyether polyol and so on, and these polyol products are the downstream products of oil, resource dependence is strong, prices is high, process safety is poor. Therefore, it is an important trend for developing bio-based raw materials to substitute petrochemical resources, develop bio-based polyols, improve product quality, reduce resource dependence and improve process safety.

Vegetable oil polyol is an important renewable resource, it can react with isocyanates compound and produce polyurethane, it is a good alternative of petroleum-based polyol raw materials. In recent years, methods of synthetic vegetable oil polyols are: 1) alcoholysis the vegetable oil and polyol, produce polyhydroxy compound; 2) oxidation unsaturated double bond of vegetable oil by using ozone, produce polyhydroxy compound of hydroxyl group which contain end position. 3) oxidizing the vegetable oil to an epoxy vegetable oil and then producing polyhydroxy compound by hydrolysis, hydrogenation, methyl esterification or halogenation.

The synthetic vegetable oil polyol process, method 3) which is the epoxy ring opening method for the preparation of vegetable oil polyol is low cost, is currently recognized as the most likely in the polyurethane industry to achieve the industrialization method, and usually combined with the method 1). CN1837180A and CN101139252A, respectively, using rapeseed oil and jatropha oil as main raw materials to prepare the vegetable oil polyol by alcoholysis/epoxidation/ring-opening three steps reaction. CN1837181A and CN101108803A, respectively, using rapeseed oil and jatropha oil as main raw materials to prepare the vegetable oil polyol by epoxidation/ring opening/alcoholysis three steps reaction. CN1907944A epoxidized rapeseed oil is used as the main raw material, and the vegetable oil polyol is prepared by the two steps reaction of ring opening and alcoholysis. CN 101314632A discloses "a method for the preparation of rigid polyurethane foams by using soybean oil", which comprises four steps, which are epoxidation/ring opening/alcoholysis/esterification. CN101906016A discloses "a rubber seed oil polyol and a preparation method thereof", the rubber seed oil is used as the main raw material to obtain the vegetable oil polyol through the epoxidation/ring-opening two steps reaction. CN102206154A discloses "a vegetable oil polyol and method for the preparation thereo", including epoxidation and ring-opening two steps reaction.

The patented preparation of vegetable oil polyols are synthesized through batch reactor, epoxidation and open-loop is divided into two steps, there are the following disadvantages: ① long reaction time; ② high energy consumption; ③ low level of equipment and automatic control; ④ Unavoidable side effects lead to lower product quality (oligomerization side effects lead to low hydroxyl value of the product, the viscosity is too large).

In addition, the product of the vegetable oil polyols based on epoxidized/open-ring and even epoxidized/open-ring/alcoholysis or alcoholysis/epoxidation/ring-opening reaction are still common low hydroxyl value, quality is not high, when using for polyurethane materials, a certain percentage of petrochemical-based polyols are still needed.

Based on the said problems, the present invention overcomes the shortcomings of the prior art, designs a new synthetic route and combines the new production technology to synthesize a vegetable oil polyol, which are novel structure and high quality, can completely replace the traditional petrochemical base polyol and apply in the polyurethane foam materials.

SUMMARY

The technical problem to be solved by the present invention is to provide a vegetable oil polyol, in order to solve the problem of low hydroxyl value and low quality in the prior art.

Another technical problem to be solved by the present invention is to provide the said preparation method of the vegetable oil polyol.

The last technical problem to be solved by the present invention is to provide the application of the said vegetable oil polyol in the preparation of polyurethane foam material.

In order to solve the said technical problem, the present invention uses the following technical solutions:

A preparation method of vegetable oil polyol, it comprises the steps of:

(1) Oxidating the allyl of vegetable oil, introducing secondary hydroxyl group;

(2) Simultaneously pumped the product obtained in the step (1) and the epoxy-hydroxylation reagent into the micro flow reactor for reaction;

(3) Collecting the organic phase in the product obtained in step (2), washing and drying to obtain vegetable oil polyol.

In the step (1), the vegetable oils are any one or combination of olive oil, peanut oil, rapeseed oil, cottonseed oil, soybean oil, coconut oil, palm oil, sesame oil, sunflower oil, linseed oil, castor oil, tung oil, rice bran oil and corn oil.

In the step (1), the method of oxidating the allyl of vegetable oil and introducing secondary hydroxyl group is dissolving vegetable oil into organic solvent, adding allylic oxidant, uniformly mixing, stirring at 35-55° C. for 25-45 h, adding $Na_2CO_3$ saturated aqueous solution, cooling, adding $Na_2SO_3$ and stirring, separating organic phase, and then the organic phase was washed and dried.

In the step (1), the molar ratio of the vegetable oil and the organic solvent is 1:50~70, and the volume ratio of the organic solvent and $Na_2CO_3$ saturated aqueous solution is 3~1:1; wherein, the organic solvent is ethyl acetate or tetrahydrofuran, the allylic oxidant is selenium dioxide and/or tert-Butyl hydroperoxide.

In the step (1), when the allylic oxidant is selenium dioxide, the molar ratio of selenium dioxide to vegetable oil double bond is 0.3~0.6:1; when the allylic oxidant is tert-Butyl hydroperoxide, the molar ratio of the tert-Butyl hydroperoxide to vegetable oil double bond is 0.8~2.8:1; when the allylic oxidants are selenium dioxide and tert-Butyl hydroperoxide, the molar ratio of selenium dioxide to tert-Butyl hydroperoxide is 0.2~0.5:1, and the molar ratio of selenium dioxide to the vegetable oil double bond is 0.1~0.2:1.

In the step (1), The epoxy-hydroxylation reagent includes the following components: hydrogen peroxide, formic acid, sulfuric acid and ethylenediamine tetraacetic acid disodium; wherein, the molar ratio of hydrogen peroxide to formic acid is 1:1, the molar ratio of formic acid, sulfuric acid and ethylenediamine tetraacetic acid disodium to the vegetable oil is 7~16:0.02~0.2:0.01~0.2:1.

In the step (1), the purpose of adding $Na_2SO_3$ is to remove the excess allylic oxidant, the addition of $Na_2SO_3$ can completely remove excess allylic oxidant is better.

In the step (2), the reaction temperature in the micro flow field reactor is 60~120° C., and the duration of stay for material is 4~13 min.

In the step (2), the said micro flow field reactor is a micro channel modular reaction apparatus, which comprises a micro mixer, a microstructure heat exchanger and a microstructure reactor which are pipeline connected in turn; wherein, the micro mixer is pipeline connected with two accurate and low-pulsation feed pumps, one pump is responsible for pumping the vegetable oil, and the other pump is responsible for pumping the pre-mixed epoxy-hydroxylation reagent.

Wherein, the said micro mixer model is preferable slit plate mixer LH25, microstructure heat exchanger model is preferable coaxial heat exchanger, microstructure reactor model is perferable sandwich reactor HC or homemade Hastelloy micro channel reactor.

In the step (2), washing method is using 5% sodium carbonate aqueous solution to wash until neutral, drying method is using anhydrous sodium sulfate.

The equation of the step (2) is as follows:

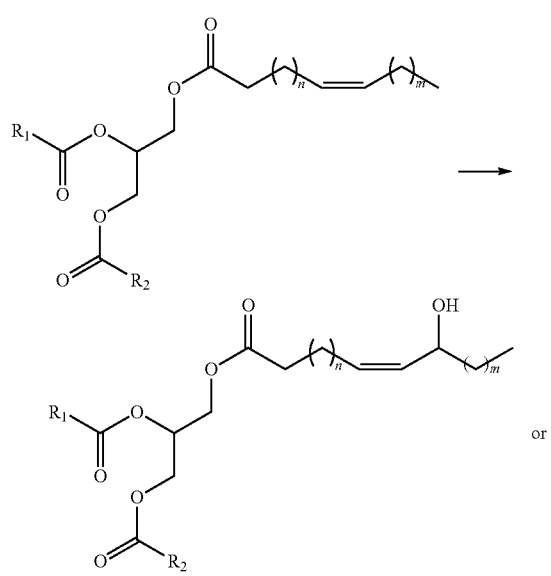

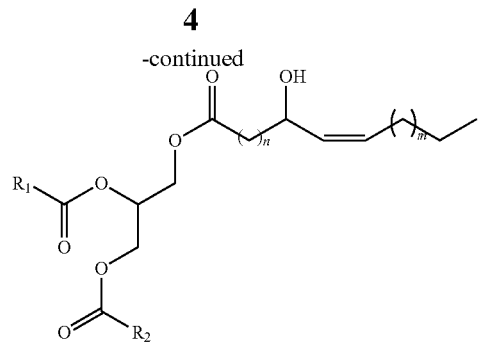

The structural formula of the vegetable oil polyol obtained in the step (2) is as follows:

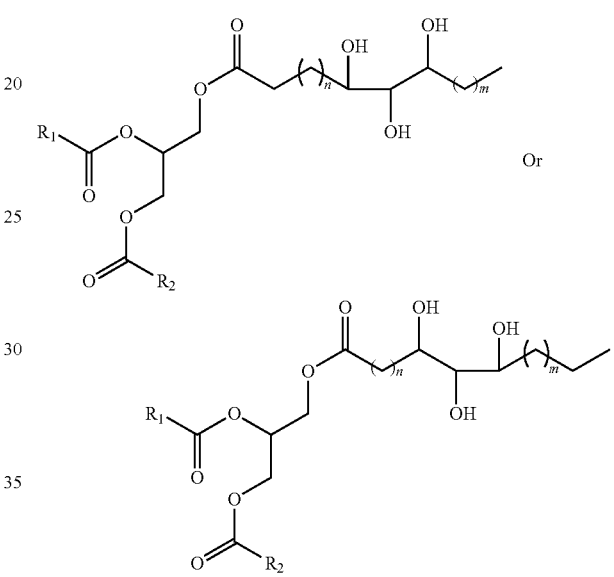

The vegetable oil polyol prepared by the said production method is also within the scope of the present invention.

The application of the said vegetable oil polyols in the preparation of polyurethane foams is also within the scope of the present invention.

Advantageous effects: Compared with the method of preparing vegetable oil polyol by epoxidation and then re-ring opening of vegetable oil in the prior report, the present invention creatively discloses pre-oxidation treatment of the vegetable oil allylic position, increases the content of hydroxyl groups in the product, depending on the micro flow field technology to achieve the following one step operation process of epoxidation and ring-opening reaction, the vegetable oil polyol product is novel structure, high hydroxyl value, can be applied to the preparation of polyurethane foam; At the same time, choosing micro flow field technology may reduce side reaction, improve product quality, and achieve energy saving also.

DETAILED DESCRIPTION

Figure 1:
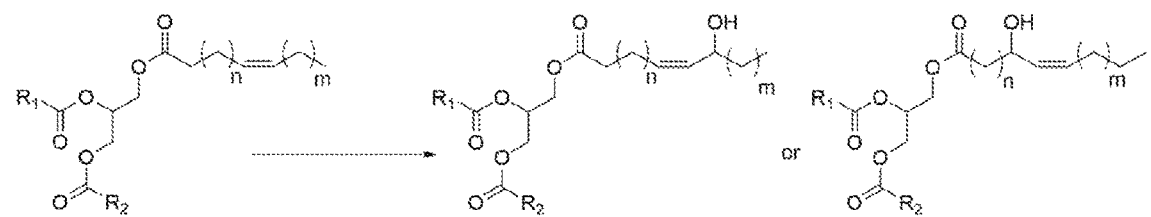
FIG. 1 is the reaction of allylic oxidation of vegetable oil.
Figure 2:
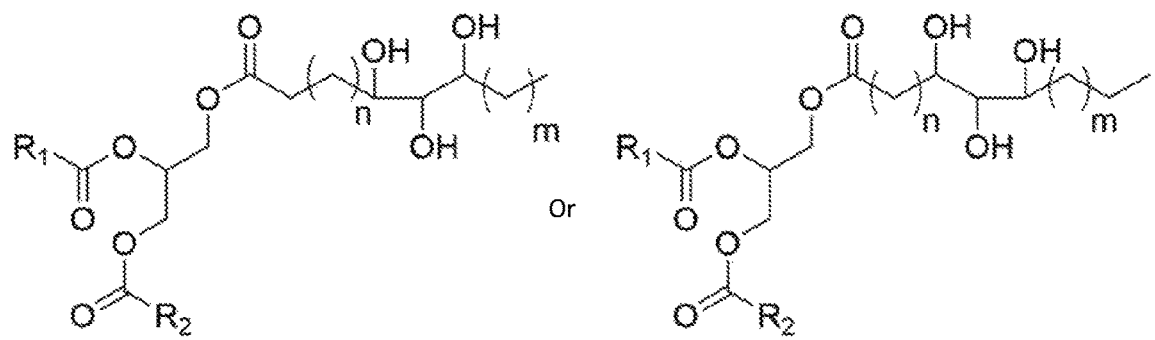
FIG. 2 is the present invention structural formula of the vegetable oil polyol.

The present invention will be better understood from the following examples. However, those skilled in the art will recognize many variations that are within the spirit of the invention and scope of the claims.

The relative measurement of the prepared vegetable oil polyol and the polyurethane foam in the following examples is as follows:

According to GB/T12008.3-2009 to measure hydroxyl value;
According to GB/T12008.7-2010 to measure viscosity;
According to GB/T 6343-2009 to measure the apparent density; According to GB/T 8813-2008 to measure the compressive strength of rigid foam, take the vertical cross-section of the foam as compression surface, the compression rate is 5 mm/min, 10% of the sample deformation of the test value as the material compressive strength.

The micro channel modular reaction used in the following examples is a micro mixer (model slit plate mixer LH25), a microstructure heat exchanger (model coaxial heat exchanger) and a microstructure reactor which are pipeline connected, the micro mixer is also connected by piping with two precision and low-pulsation feed pumps.

Embodiment 1

100 g of soybean oil is dissolved in 670 mL of ethyl acetate and 18.9 g of selenium dioxide is added thereto. after mixing, the reaction mixture is stirred at 40° C. for 30 h, followed by cooling with a saturated aqueous solution of 332 mL of $Na_2CO_3$, and then an appropriate amount of $Na_2SO_3$ is added to remove the excess oxidant, followed by separation of the organic phase and is washed three times with saturated aqueous sodium chloride, dried it by anhydrous magnesium sulphate to obtain allylic oxidation vegetable oil. Combined the oxidized vegetable oil with an epoxy-hydroxylating agent (98% formic acid, 186.8 g, 30% $H_2O_2$ 450.9 g, 98% sulfuric acid 1.7 g, ethylenediamine tetraacetic acid disodium 4.2 g) at the same time pumped into the micro channel modular reaction apparatus (microstructure reactor model is sandwich reactor HC), the flow rate is 0.8 mL/min, 4.9 mL/min, keeping at 70° C. and normal pressure for 6.5 min, finally collecting the organic phase in the product, washing with 5% sodium carbonate aqueous solution until to neutral, drying with anhydrous sodium sulfate, and obtaining vegetable oil polyol, the hydroxyl value is 420 mgKOH/g and the viscosity is 8050 mPa·s.

Embodiment 2

100 g of peanut oil is dissolved in 670 mL of tetrahydrofuran and 17.5 g of selenium dioxide is added thereto. after mixing, the reaction mixture is stirred at 45° C. for 35 h, followed by cooling with a saturated aqueous solution of 335 mL of $Na_2CO_3$, and then an appropriate amount of $Na_2SO_3$ is added to remove the excess oxidant, followed by separation of the organic phase and is washed three times with saturated aqueous sodium chloride, dried it by anhydrous magnesium sulphate to obtain allylic oxidation vegetable oil. Combined the oxidized vegetable oil with an epoxy-hydroxylating agent (98% formic acid, 169 g, 30% $H_2O_2$ 407.9 g, 98% sulfuric acid 1.8 g, ethylenediamine tetraacetic acid disodium 6.7 g) at the same time pumped into the micro channel modular reaction apparatus (microstructure reactor model is homemade Hastelloy micro channel reactor), the flow rate is 0.3 mL/min, 1.9 mL/min, keeping at 60° C. and normal pressure for 9 min, finally collecting the organic phase in the product, washing with 5% sodium carbonate aqueous solution until to neutral, drying with anhydrous sodium sulfate, and obtaining vegetable oil polyol, the hydroxyl value is 378 mgKOH/g and the viscosity is 7150 mPa·s.

Embodiment 3

100 g of cottonseed oil is dissolved in 670 mL of ethyl acetate and 89.6 g of tert-Butyl hydroperoxide is added thereto. after mixing, the reaction mixture is stirred at 50° C. for 40 h, followed by cooling with a saturated aqueous solution of 335 mL of $Na_2CO_3$, and then an appropriate amount of $Na_2SO_3$ is added to remove the excess oxidant, followed by separation of the organic phase and is washed three times with saturated aqueous sodium chloride, dried it by anhydrous magnesium sulphate to obtain allylic oxidation vegetable oil. Combined the oxidized vegetable oil with an epoxy-hydroxylating agent (98% formic acid, 210.2 g, 30% $H_2O_2$ 507.3 g, 98% sulfuric acid 4.0 g, ethylenediamine tetraacetic acid disodium 18.5 g) at the same time pumped into the micro channel modular reaction apparatus (microstructure reactor model is sandwich reactor HC), the flow rate is 0.5 mL/min, 3.2 mL/min, keeping at 90° C. and normal pressure for 10 min, finally collecting the organic phase in the product, washing with 5% sodium carbonate aqueous solution until to neutral, drying with anhydrous sodium sulfate, and obtaining vegetable oil polyol, the hydroxyl value is 392 mgKOH/g and the viscosity is 7800 mPa·s.

Embodiment 4

100 g of palm oil is dissolved in 670 mL of tetrahydrofuran and 5.3 g of selenium dioxide and 21.3 g of tert-Butyl hydroperoxide are added thereto. after mixing, the reaction mixture is stirred at 36° C. for 45 h, followed by cooling with a saturated aqueous solution of 335 mL of $Na_2CO_3$, and then an appropriate amount of $Na_2SO_3$ was added to remove the excess oxidant, followed by separation of the organic phase and is washed three times with saturated aqueous sodium chloride, dried it by anhydrous magnesium sulphate to obtain allylic oxidation vegetable oil. Combined the oxidized vegetable oil with an epoxy-hydroxylating agent (98.8% formic acid, 111.2 g, 30% $H_2O_2$ 268.4 g, 98% sulfuric acid 3.6 g, ethylenediamine tetraacetic acid disodium 13.2 g) at the same time pumped into the micro channel modular reaction apparatus (microstructure reactor model is homemade Hastelloy micro channel reactor), the flow rate is 1.0 mL/min, 3.4 mL/min, keeping at 110° C. and normal pressure for 4.5 min, finally collecting the organic phase in the product, washing with 5% sodium carbonate aqueous solution until to neutral, drying with anhydrous sodium sulfate, and obtaining vegetable oil polyol, the hydroxyl value is 313 mgKOH/g and the viscosity is 5050 mPa·s.

Embodiment 5

Performance test of polyurethane rigid foam prepared from vegetable oil polyol.

The soybean oil polyol prepared in Example 1 is subjected to a one step foaming process, reacting with the foam stabilizer AK-8803 (Nanjing Meiside), cyclohexylamine (Jiangdu Dajiang Chemical), isocyanate WANNATE® PM-200 (Yantai Wanhua) and foaming agent cyclopentane (Foshan Meilong). The apparent density of the polyurethane foam is 37.6 kg/m3 and the vertical compressive strength is 207 kPa.

Embodiment 6

The embodiment is as the same as Example 1, except that the saturated aqueous $Na_2CO_3$ solution is 670 mL.

Embodiment 7

The embodiment is as the same as Example 1, except that the saturated aqueous $Na_2CO_3$ solution is 230 mL.

What is claimed is:

1. A preparation method of vegetable oil polyol, characterized in that, it comprises the steps of:
   (1) oxidating an allyl group of a vegetable oil with an allylic oxidant for introducing a secondary hydroxyl group into the vegetable oil; wherein the allylic oxidant is a selenium dioxide, or a tert-Butyl hydroperoxide, or a combination of selenium dioxide and tert-Butyl hydroperoxide;
   (2) simultaneously pumping the product obtained in the step (1) and an epoxy-hydroxylation reagent into a micro flow reactor for reaction;
   (3) collecting an organic phase in the product obtained in step (2), washing and drying to obtain vegetable oil polyol.

2. The preparation method according to claim 1, characterized in that, in the step (1), the vegetable oils are any one or combination of olive oil, peanut oil, rapeseed oil, cottonseed oil, soybean oil, coconut oil, palm oil, sesame oil, sunflower oil, linseed oil, castor oil, tung oil, rice bran oil and corn oil.

3. The preparation method according to claim 2, characterized in that, in the step (1), the method of oxidating the allyl group of vegetable oil and introducing the secondary hydroxyl group is dissolving the vegetable oil into an organic solvent, adding the allylic oxidant, uniformly mixing, stirring at 35-55° C. for 25-45 h, adding $Na_2CO_3$ saturated aqueous solution, cooling, adding $Na_2SO_3$ and stirring, separating organic phase, and then the organic phase was washed and dried.

4. The preparation method according to claim 3, characterized in that, in the step (1), the molar ratio of the vegetable oil and the organic solvent is 1:50-70, and the volume ratio of the organic solvent and $Na_2CO_3$ saturated aqueous solution is 3~1:1; wherein, the organic solvent is ethyl acetate or tetrahydrofuran, the allylic oxidant is selenium dioxide or tert-Butyl hydroperoxide or a mixture of selenium dioxide and tert-Butyl hydroperoxide.

5. The preparation method according to claim 4, characterized in that, in the step (1), when the allylic oxidant is selenium dioxide, the molar ratio of selenium dioxide to vegetable oil double bond is 0.3~0.6:1; when the allylic oxidant is tert-Butyl hydroperoxide, the molar ratio of the tert-Butyl hydroperoxide to vegetable oil double bond is 0.8~2.8:1; when the allylic oxidant is the mixture of selenium dioxide and tert-Butyl hydroperoxide, the molar ratio of selenium dioxide to tert-Butyl hydroperoxide is 0.2~0.5:1, and the molar ratio of selenium dioxide to the vegetable oil double bond is 0.1~0.2:1.

6. The preparation method according to claim 1, characterized in that, in the step (2), the epoxy-hydroxylation reagent includes hydrogen peroxide, formic acid, sulfuric acid and ethylenediamine tetraacetic acid disodium; wherein, the molar ratio of hydrogen peroxide to formic acid is 1:1, the molar ratio of formic acid, sulfuric acid and ethylenediamine tetraacetic acid disodium to the vegetable oil is 7~16:0.02~0.2:0.01~0.2:1.

7. The preparation method according to claim 1, characterized in that, in the step (2), the reaction temperature in the micro flow reactor is 60~120° C., and the duration of stay for material is 4~13 min.

8. The preparation method according to claim 1, characterized in that, in the step (2), the micro flow field reactor is a micro channel modular reaction apparatus, which comprises a micro mixer, a microstructure heat exchanger and a microstructure reactor are pipeline connected in turn; wherein, the micro mixer is pipeline connected with two feed pumps.

* * * * *